United States Patent

Bollens et al.

Patent Number: 6,017,547
Date of Patent: Jan. 25, 2000

[54] HYDROFLUOROCARBON COMPOUNDS AND THEIR USE IN COSMETIC COMPOSITIONS

[75] Inventors: Eric Bollens, Saint-Maurice; Claude Mahieu, Paris, both of France

[73] Assignee: L'Oreal, Paris, France

[21] Appl. No.: 08/795,162

[22] Filed: Feb. 10, 1997

Related U.S. Application Data

[63] Continuation of application No. 08/379,460, filed as application No. PCT/FR94/00635, Jun. 1, 1994, abandoned.

[30] Foreign Application Priority Data

Jun. 2, 1993 [FR] France ................... 93 06606

[51] Int. Cl.$^7$ ............... A61K 6/00; A61K 7/00; A61K 7/06
[52] U.S. Cl. ........................... 424/401; 424/70.1
[58] Field of Search ............................ 424/70.1

[56] References Cited

U.S. PATENT DOCUMENTS

| | | | |
|---|---|---|---|
| 4,126,702 | 11/1978 | Vanlerberghe et al. | 424/365 |
| 4,584,196 | 4/1986 | Vanlerberghe et al. | 424/70 |
| 4,880,620 | 11/1989 | Vanlerberghe et al. | 424/70 |

FOREIGN PATENT DOCUMENTS

| | | |
|---|---|---|
| 0 010 523 | 4/1980 | European Pat. Off. . |
| 2 416 222 | 8/1979 | France . |
| 2 516 920 | 5/1983 | France . |
| WO 93/11103 | 6/1993 | WIPO . |

*Primary Examiner*—Thurman K. Page
*Assistant Examiner*—Sharon Howard
*Attorney, Agent, or Firm*—Jacobson, Price, Holman & Stern, PLLC

[57] ABSTRACT

The present invention concerns hydrofluorocarbon compound with formula (I):

$$R_F—(CH_2)_n—X—[C_3H_5(OH)]—(Y)_x—R_H \quad (I)$$

where $C_3H_5(OH)$ represents the structures:

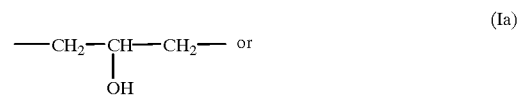

(Ia)

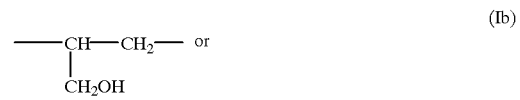

(Ib)

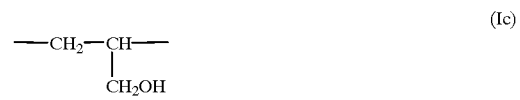

(Ic)

$R_F$ represents a perfluorinated, linear or branched $C_4$–$C_{20}$ alkyl radical or a mixture of perfluorinated, linear or branched $C_4$–$C_{20}$ alkyl radicals;

$R_H$ represents a linear or branched $C_{23}$–$C_{36}$ alkyl radical or a mixture of linear or branched $C_{23}$–$C_{36}$ alkyl radicals;

n is between 0 and 4;

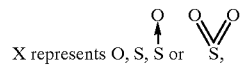

X represents O, S, S or S, x is 0 or 1;

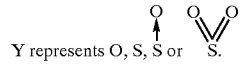

Y represents O, S, S or S.

It also concerns their use in cosmetic compositions and cosmetic compositions containing these compounds.

9 Claims, No Drawings

HYDROFLUOROCARBON COMPOUNDS AND THEIR USE IN COSMETIC COMPOSITIONS

This application is a continuation of application Ser. No. 08/379,460, filed Mar. 21, 1995, now abandoned which is a 371 of PCT/FR94/00635 filed Jun. 01, 1994.

The present invention concerns hydro- and fluorocarbon compounds for use in cosmetic compositions, and cosmetic compositions containing these compounds.

Perfluoropolyethers are known for their use in cleaning, protecting or making up the skin, or for washing hair. These compounds are known to have a low surface tension and are easy to spread, but have very low solubility in most fluids apart from fluorine-containing fluids. This means that they are difficult to incorporate into cosmetic composition formulations. Some of these compounds, perfluoromethylisopropylethers, are sold by MONTEFLUO under the trade name "FOMBLIN HC".

We have now discovered compounds which, contrary to FOMBLIN compounds, have good solubility, in particular in the conventional solvents used in cosmetics, such as low alcohols, fatty substances and the usual oils. Their amphiphilic character, properties and compatibility with the solvents mean that homogeneous, stable compositions can be prepared and, for example, can ensure that the emulsions they form have good stability.

The present invention thus concerns the use of compounds with formula:

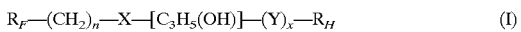 (I)

where $C_3H_5(OH)$ represents the structures:

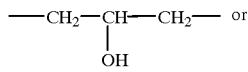 or (Ia)

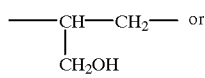 or (Ib)

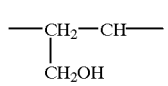 (Ic)

$R_F$ represents a perfluorinated, linear or branched $C_4$–$C_{20}$ alkyl radical or a mixture of perfluorinated, linear or branched $C_4$–$C_{20}$ alkyl radicals;

$R_H$ represents a linear or branched $C_{23}$–$C_{36}$ alkyl radical or a mixture of linear or branched $C_{23}$–$C_{36}$ alkyl radicals;

n is between 0 and 4;

x is 0 or 1;

Preferred compounds are those for which $R_F$ represents a perfluorinated $C_6$–$C_{10}$ alkyl radical, $R_H$ represents a linear or branched $C_{23}$–$C_{30}$ alkyl radical, n equals 2, and x equals 1.

Preferably, X represents S and Y represents O.

Examples of linear or branched alkyl radicals are 2-decyl-tetradecyl, 2-dodecyl-hexadecyl and 2-hexadecyleicosyl radicals.

Compounds with formula (I) in accordance with the invention can be prepared by reacting a fluorine compound containing an acidic hydrogen with formula (II):

 (II)

with an epoxide with formula (III):

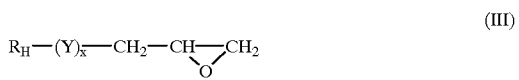 (III)

or by reacting a hydrocarbon containing an acidic hydrogen with formula (IV):

 (IV)

with a fluorine-containing epoxide with formula (V):

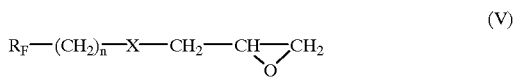 (V)

in the presence of an acidic or basic compound which acts as a reactant or as a catalyst, to produce the corresponding compound with formula (I). Substituents $R_F$, $R_H$, n and x have the same meanings in formulae (II), (III), (IV) and (V) as those given for formula (I), and X and Y represent O or S.

The mercaptan function can optionally be oxidized to the sulfoxide or sulfone using an oxidizing agent, preferably hydrogen peroxide in an acidic medium.

Compounds with formula (V) are described in United States patent U.S. Pat. No. 3,976,698, in European patent application EP-A-0 300 358 and in German patent application DE-A-2 018 461.

When X represents S in formula (II) or (IV), a basic compound is preferably used.

The compounds which act as a reactant or as a catalyst may thus be basic, such as alkali metals, alkali or alkaline earth metal hydroxides, alkali metal alcoholates such as methylates or tertiobutylates, alkaline hydrides such as sodium hydride, or tertiary amines such as pyridine or triethylamine. They may also be Lewis bases, for example cesium, rubidium or potassium fluoride. These compounds may be supported on a solid support such as alumina. Preferably, an alkali alcoholate such as sodium methylate or a tertiary amine such as pyridine is used.

These compounds may also be acids, in particular when the starting material with formula (II) or (IV) is an alcohol. These acids may be mineral acids or their tertiary amine salts, or Lewis acids such as boron trifluoride, tin tetrachloride, or antimony pentachloride, used neat, in solution or associated with any normal support.

The concentration of acidic or basic compounds acting as reactant or catalyst and used in preparing compounds with formula (I) can be between 1% and 100% molar, preferably between 2% and 10% molar with respect to the fluorine-containing compound containing an acidic hydrogen with formula (II) or (IV).

The preparation can be carried out in the presence or absence of a solvent.

Examples of solvents are aliphatic hydrocarbons such as heptane or hexane, cyclic hydrocarbons such as cyclohexane, aromatic hydrocarbons such as toluene, ethers such as ethyl ether or isopropyl ether or tert-butyl-methylether, cyclic ethers such as dioxane, or acetonitrile, dimethylformamide, N-methylpyrrolidone, or dimethylacetamide.

When the compound with formula (II) or (IV) is a thiol (X=S), alcohols such as methanol, ethanol or isopropanol can be used as a solvent.

The compound of the invention can be prepared by firstly mixing the compound containing an acidic hydrogen with formula (II) or (IV) with the acidic or basic reactant or catalyst, in an inert atmosphere. Mixing can be carried out at a temperature of between 20° C. and 180° C., preferably between 50° C. and 150° C. The term "inert atmosphere" means an atmosphere of nitrogen, argon or helium, for example.

Mixing can be effected in the presence or absence of a solvent, depending on the nature of the compound containing an acidic hydrogen and the reactant or catalyst.

The epoxide with formula (III) or (V) is then added to the mixture obtained. Addition can be effected all at once or gradually, over a period of 30 minutes to 2 hours, for example.

The reaction time is thus between about 1 hour and 24 hours, preferably between 1 hour and 3 hours.

When it contains a mercaptan function, the compound produced by the reaction can be oxidized to a sulfoxide or sulfone in the presence of hydrogen peroxide in an acidic medium, using known methods, particularly as described in French patents FR-A-2 099 092 and FR-A-2 516 920.

It may also be necessary to neutralize the mixture obtained, and separate the synthesized compound using conventional methods, for example distillation.

When a compound with formula (I) is prepared in the presence of a basic compound it produces only compounds in which $C_3H_5(OH)$ represents group (Ia). When the reaction is carried out in the presence of an acidic compound a mixture of compounds can be obtained corresponding to designations (Ia), (Ib) and (Ic) of $C_3H_5(OH)$.

The compound of the invention can be in the form of an oil or it may be solid at room temperature.

The invention further concerns the use of products with formula (I), amphiphilic compounds, in cosmetic compositions.

In general, these compounds are used in cosmetic compositions to improve the cosmetic properties. They provide smoothness, gloss and a non-sticky feel to keratinous material such as skin, hair and nails.

The invention thus also concerns a cosmetic composition characterized in that it contains at least one compound with formula (I) as defined above.

The composition can be in the form of an emulsion, milk or cream, oily or oleoalcoholic lotion, oily or oleoalcoholic gel, ionic or non-ionic amphiphilic lipid based vesicular dispersion, solid stick, paste, spray or aerosol foam.

Depending on the form of the composition into which the compound of the invention is incorporated, the compositions also contain additives which are normal for the selected form.

More precisely, the composition can be a milk or cream for skin or hair, a make-up removing cream, lotion or milk, a sun protection cream, gel, milk or lotion, a shaving cream or foam, an aftershave lotion, a shampoo or conditioner, a body deodorant, a toothpaste, a lacquer, a styling gel, a direct hair dye composition, a hair perming composition, a lip care product or a nail care product.

The cosmetic composition can also be used as make-up for eyelashes, eyebrows, nails, lips or for skin in epidermal treatments, a foundation, lipstick, eye-shadow, blusher, eyeliner, mascara or nail polish, for example.

Compounds with formula (I) represent 0.1% to 25%, preferably 0.1% to 15% of the total composition weight.

Examples of normal cosmetic additives which can be present in this type of composition are the usual fatty substances, organic solvents, silicones, thickeners, softeners, UV-A or UV-B or broad spectrum solar filters, anti-foaming agents, moisturising agents, humectants, fragrances, preservatives, surfactants, fillers, sequestrating agents, emulsifiers, anionic, cationic, non-ionic or amphoteric polymers and their mixtures, antiperspirants, alkalinizing agents, dyes, pigments, propellants, anti-oxidizing agents and free radical absorbers.

More precisely, examples of fatty substances are oils or waxes or their mixtures, fatty acids, fatty alcohols, fatty acid esters such as $C_6$ to $C_{18}$ fatty acid triglycerides, vaseline, paraffin, lanolin, or hydrogenated or acetylated lanolin.

Examples of oils are mineral, animal, vegetable or synthetic oils, in particular vaseline oil, paraffin oil, castor oil, jojoba oil, sesame seed oil, and silicone and isoparaffin oils and gums.

Particular examples of animal, fossil, vegetable, mineral or synthetic waxes are beeswax, Carouba wax, Candelilla wax, ozokerites, microcrystalline waxes and silicone waxes and resins.

Examples of organic solvents which are generally used in cosmetic compositions are $C_1$ to $C_6$ low monoalcohols or polyalcohols such as ethanol, isopropanol, propyleneglycol, glycerol, sorbitol, ketones such as acetone, esters such as butyl acetate or ethyl acetate, and toluene.

Examples of thickeners are cellulose derivatives, polyacrylic acid derivatives, guar gum or carouba gum, and xanthane gum.

Examples of surfactants are non-ionic surfactants such as alkyl($C_8$–$C_{24}$)polyglycosides where the number of glucoside units is between 1 and 15, and non-ionic polyglycerolated surfactants.

Particular alkylpolyglycosides are those sold under the trade name APG, such as APG 300, APG 350, APG 500, APG 550, APG 625 and APG base 10–12; and products sold by SEPPIC under the trade names TRITON CG 110 and TRITON CG 312.

The polyglycerolated compounds are derivatives resulting from condensation of 1 to 10, preferably 2 to 6 moles of glycidol with one mole of $C_{10}$–$C_{14}$ alcohol or alphadiol, or with $C_{12}$–$C_{18}$ fatty acid diglycolamides, such as those described in French patents FR-A-1 477 048, FR-A-2 328 763, FR-A-2 091 516 and FR-A-2 169 787.

The vesicular dispersions of ionic or non-ionic amphiphilic lipids mentioned above can be prepared using normal techniques, for example as described in "Les liposomes en biologie cellulaire et pharmacologie", Ed. INSERM/John Libbery Eurotext (1987), pp 6–18.

For toothpaste compositions, the usual additives can be used such as polishing agents for example silica, active ingredients such as fluorides, for example sodium fluoride, and optional sweetening agents, for example sodium saccharinate.

The following examples illustrate the invention and do not in any way limit its scope.

PREPARATION EXAMPLES

Example I

Preparation of 1-(2'-F-octylethylthio)-3-(2"-decyltetradecyloxy)-2-propanol 40 g of a methanolic solution of sodium methylate (about 30%—5.65 meq $g^{-1}$) was weighed into a 1 liter reactor in a stream of nitrogen. 130 ml of absolute methanol was added.

The temperature was reduced to 2° C., and 96 g of 2-F-octylethanethiol (0.2 mole) was added over 30 minutes, maintaining the temperature at 2° C.

89.45 g of 1-(2'-decyltetradecyloxy)-3-chloro-2-propanol was added over 20 minutes, at the same temperature.

The ice bath was removed. When the mixture had reached a temperature of 20° C. it was refluxed for 3 hours.

After cooling to 25° C., the mixture was filtered through no 4 sintered glass, then transferred to a separating funnel and the lower phase was recovered which proved to be the 1-(2'-F-octylethylthio)-3-(2"-decyltetradecyloxy)-2-propanol (150 g—80%).

The product was purified on a silica column (heptane/ethyl acetate eluent).

A light amber oil was obtained.

| Elemental analysis: | | | | |
|---|---|---|---|---|
| | % C | % H | % S | % F |
| Calculated | 49.88 | 6.68 | 3.6 | 36.25 |
| Measured | 50.07 | 6.72 | 3.28 | 36.06 |

Example II

Preparation of 1-(2'-F-octylethylthio)-3-(2"-dodecylhexadecyloxy)-2-propanol 20 g of a methanolic solution of sodium methylate (about 30%—5.65 meq $g^{-1}$) was weighed into a 1 liter reactor in a stream of nitrogen. 130 ml of absolute methanol was added.

The temperature was reduced to 2° C. and 48 g of 2-F-octylethanethiol (0.1 mole) was added over 20 minutes, maintaining the temperature at 2° C.

50.25 g of 1-(2'-dodecylhexadecyloxy)-3-chloro-2-propanol was added over 15 minutes at the same temperature.

The ice bath was removed. When the mixture had reached a temperature of 20° C. it was refluxed for 3 hours.

After cooling to 25° C. the mixture was filtered through n° 4 sintered glass and then transferred to a separating funnel and the lower phase was recovered which proved to be the 1-(2'-F-octylethylthio)-3-(2"-dodecylhexadecyloxy)-2-propanol (66 g—70%).

The product was purified on a silica column (heptane/ethyl acetate eluent).

A beige wax was obtained which had a melting point of 30° C.

| Elemental analysis: | | | | |
|---|---|---|---|---|
| | % C | % H | % S | % F |
| Calculated | 52.00 | 7.17 | 3.39 | 34.1 |
| Measured | 59.84 | 7.06 | 3.66 | 33.9 |

FORMULATION EXAMPLES

Example 1

Skin Cream—Oil-in-Water Emulsion

A skin cream was prepared in the form of an oil-in-water emulsion, with the following composition:

| Phase A | |
|---|---|
| Non-ionic hydroxypropylether surfactant obtained by condensation, with alkaline catalysis, of 3.5 moles of glycidol with a mixture of $C_{11}$–$C_{14}$ alphadiols, in accordance with French patent FR-A-2 091 516 | 2.4 g |
| Methyl parahydroxybenzoate | 0.2 g |
| Glycerine | 5 g |
| Water | 22.06 g |
| Phase A' | |
| Gel of glyceryl polyacrylate in water (50/50), sold by HISPANO CHEMICA under the trade name HISPAGEL 100 | 56.14 g |
| Phase B | |
| Cetyl alcohol | 1 g |
| Compound of Example I | 5 g |
| Apricot kernel oil | 5 g |
| Sesame seed oil | 1.5 g |
| Caprylic/capric acid triglyceride, sold by HULS under the trade name MIGLYOL 812 | 1.5 g |
| Propyl parahydroxybenzoate | 0.2 g |

Method

Phase A was heated to 80° C. Phase A' was added with stirring followed by phase B which had been heated to 80° C. The mixture was allowed to cool to room temperature, maintaining the stirring.

Example 2

Skin Cream—Oil-in-Water Emulsion

A skin cream was prepared in the form of an oil-in-water emulsion with the following composition:

| Phase A | |
|---|---|
| Non-ionic hydroxypropylether surfactant obtained by condensation, with alkaline catalysis, of 3.5 moles of glycidol with a mixture of $C_{11}$–$C_{14}$ alphadiols, in accordance with French patent FR-A-2 091 516 | 2.4 g |
| Methyl parahydroxybenzoate | 0.2 g |
| Glycerine | 5 g |
| Water | 22.06 g |
| Phase A' | |
| Gel of glyceryl polyacrylate in water (50/50), sold by HISPANO CHEMICA under the trade name HISPAGEL 100 | 56.14 g |
| Phase B | |
| Cetyl alcohol | 1 g |
| Compound of Example II | 5 g |
| Apricot kernel oil | 5 g |
| Sesame seed oil | 1.5 g |
| Caprylic/capric acid triglyceride, sold by HULS under the trade name MIGLYOL 812 | 1.5 g |
| Propyl parahydroxybenzoate | 0.2 g |

Method

Phase A was heated to 80° C. Phase A' was added with stirring followed by phase B which had been heated to 80° C. The mixture was allowed to cool to room temperature maintaining the stirring.

EXAMPLE 3

LIPSTICK

A lipstick was prepared with the following composition:

| | |
|---|---|
| Compound of Example I | 1 g |
| Ozokerite | 14.90 g |
| Microcrystalline wax | 4.90 g |
| Candelilla wax | 7.40 g |
| Jojoba oil | 6.20 g |
| Castor oil | 1.20 g |
| Liquid lanoline | 18.60 g |
| Acetylated lanoline | 9.90 g |
| Vaseline oil | 11.10 g |
| Talc | 3.70 g |
| Micatitanium | 8.70 g |
| D&C Red n° 7 Ca lake | 5.20 g |
| D&C Red n° 7 Ba lake | 2.80 g |
| FD&C Yellow n° 5 | 1 g |
| Titanium dioxide | 3.10 g |
| Butylhydroxytoluene | 0.30 g |
| Fragrance  qs | |

The oils were mixed at a temperature of 50° C. to 60° C. The pigments and organic lacquers were ground in the oily phase.

The molten waxes were then added, followed by the talc and the micatitanium, then the fragrance.

The composition was then poured into a mold.

The lipstick was easy to apply (slid on easily) and made the lips soft.

The compound of Example I could be replaced by the compound of Example II.

EXAMPLE 4

SHAMPOO

| | |
|---|---|
| Monomethanolamine laurylether sulfate ($C_{12}/C_{14}$ 70/30), oxyethylenated with 2.2 moles of ethylene oxide, sold by MARCHON under the trade name EMPICOL EMB/3 FL | 9.8 g AM |
| Cocoylbetain, 32% in aqueous solution | 1.9 g AM |
| Hydroxyethylcellulose crosslinked with epichlorhydrine quaternized by trimethylamine, sold by NATIONAL STARCH under the trade name CELQUAT SC 240 | 0.5 g |
| Coprah acid monoisopropanolamine | 3 g |
| Glycol distearate ($C_{16}/C_{18}$ 30/70) | 2 g |
| Compound of Example I | 0.1 g |
| Preservatives, fragrance | |
| Water  qsp | 100 g |

The pH was adjusted to 5 using hydrochloric acid.

EXAMPLE 5

STYLING GEL

| | |
|---|---|
| Oil-in-water emulsion of cross-linked copolymer of acrylamide and the sodium salt of 2-acrylamido-2-methylpropanesulfonic acid, sold by SEPPIC under the trade name SEPIGEL 305 | 2 g |
| Vinylpyrrolidone/vinyl acetate (65/35) copolymer, sold by BASF under the trade name LUVISCOL VA 64 | 1 g |
| Compound of Example I | 0.2 g |
| Water  qsp | 100 g |

EXAMPLE 6

DYE COMPOSITION

| | |
|---|---|
| Oleic alcohol, polyglycerolated with 2 moles of glycerol | 4 g |
| Oleic alcohol, polyglycerolated with 2 moles of glycerol (78% AM) | 5.69 g AM |
| Oleic acid | 3 g |
| Oleic amine oxyethylenated with 2 moles of ethylene oxide, sold by AKZO under the trade name ETHOMEEN O12 | 7 g |
| Diethylaminopropyl laurylamino succinamate, sodium salt, 55% AM | 3 g AM |
| Oleic alcohol | 5 g |
| Oleic acid diethanolamide | 12 g |
| Propylene glycol | 3.5 g |
| Ethyl alcohol | 7 g |
| Dipropylene glycol | 0.5 g |
| Propyleneglycol, monomethylether | 9 g |
| Sodium metabisulfite, aqueous solution 35% AM | 0.455 g AM |
| Ammonium acetate | 0.8 g |
| Antioxidant, sequestrating agent  qs | |
| Fragrance, preservative  qs | |
| 20% ammonia solution | 10 g |
| Paraphenylenediamine | 0.18 g |
| 2-methyl-N-β-hydroxyethyl-5-aminophenol | 0.03 g |
| Para-aminophenol | 0.06 g |
| Resorcinol | 0.22 g |
| Meta-aminophenol | 0.03 g |
| N-(β-hydroxyethyl)-5-amino-4-methyl-2-amino-1-nitrobenzene | 0.01 g |
| Compound of Example I | 1 g |
| Demineralized water  qsp | 100 g |

Method

The composition was mixed weight for weight with 20 volume hydrogen peroxide.

The mixture was applied to 90% white natural gray hair.

The hair was then rinsed, washed, rinsed again and then dried.

The hair had been tinted a natural ash blond shade.

EXAMPLE 7

A toothpaste was prepared by mixing the following compounds:

| | |
|---|---|
| Compound of Example I | 0.75 g |
| Precipitated silica sold by DEGUSSA under the trade name SIDENT 22 S | 8 g |
| Precipitated silica sold by DEGUSSA under the trade name SIDENT 9 | 12 g |
| Sodium carboxymethylcellulose sold by HERCULES under the trade name BLANOSE 12 M 31 XP | 0.8 g |
| Sorbitol, 70% in aqueous solution | 44.8 g AM |
| Lauryl sulfate sold by MARCHON under the trade name EMPICOL LZV/E, 93% AM | 1.1 g AM |
| Sodium fluoride | 0.11 g |
| Sodium monofluorophosphate | 0.76 g |

EXAMPLE 7

A toothpaste was prepared by mixing the following compounds:

| | |
|---|---|
| Methyl parahydroxybenzoate | 0.25 g |
| Polyethyleneglycol, with 400 moles of ethylene oxide | 2 g |
| Sodium saccharinate | 0.15 g |
| Flavoring, preservative, dye   qs | |
| Water   qsp | 100 g |

EXAMPLE 8

DEODORANT CREAM

| | |
|---|---|
| Compound of Example I | 1 g |
| Cetylstearyl alcohol | 2 g |
| Cetylstearyl alcohol oxyethylenated with 33 moles of ethylene oxide | 0.5 g |
| 2,4,4'-trichloro-2'-hydroxydiphenyl-ether, sold by CIBA GEIGY under the trade name IRGASAN DP 300 | 0.1 g |
| Methyl parahydroxybenzoate | 0.2 g |
| Propyl parahydroxybenzoate | 0.1 g |
| Isopropyl myristate | 12 g |
| Water   qsp | 100 g |

Example 9

Perm Composition

A reducing permanent wave composition for hair was prepared by mixing the following ingredients:

| | |
|---|---|
| Thioglycolic acid | 9 g |
| Oleic acid oxyethylenated with 20 moles of ethylene oxide, sold by ICI under the trade name BRIJ 98 | 2 g |
| Compound of Example I | 0.2 g |
| Ammonia   qs   pH = 8.2 | |
| Demineralized water   qsp | 100 g |

This composition was applied to wet hair which had been set onto rollers. After leaving the composition to act for a period of 15 minutes the hair was thoroughly rinsed and then the following oxidizing composition was applied:

| | |
|---|---|
| Hydrogen peroxide   qs | 8 volumes |
| Oleic acid oxyethylenated with 20 moles of ethylene oxide, sold by ICI under the trade name BRIJ 98 | 0.5 g |
| Compound of Example I | 0.1 g |
| Citric acid   qs   pH = 3.0 | |
| Demineralized water   qsp | 100 g |

The oxidizing composition was allowed to act for about 5 minutes and then the rollers were removed and the hair was thoroughly rinsed with water.

After drying under a hood the hair had beautiful curls.

We claim:

1. A compound with formula:

     (I)

where $C_3H_5(OH)$ represents the structures:

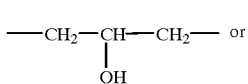     (Ia)

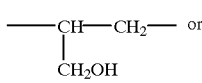     (Ib)

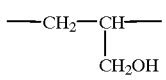     (Ic)

$R_F$ represents a perfluorinated, linear or branched $C_4$–$C_{20}$ alkyl radical $R_H$ represents a linear or branched $C_{23}$–$C_{36}$ alkyl radical;

n is between 0 and 4;

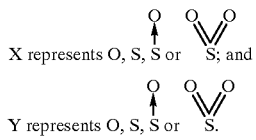

X represents O, S, S or S; and

Y represents O, S, S or S.

2. A compound according to claim 1 characterized in that:
$R_F$ represents a perfluorinated $C_6$–$C_{10}$ alkyl radical;
$R_H$ represents a linear or branched $C_{23}$–$C_{30}$ alkyl radical,
n equals 2;
X represents S; and
Y represents O.

3. A cosmetic composition containing at least one compound with formula (I):

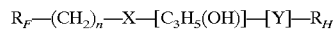     (I)

where $C_3H_5(OH)$ represents the structures:

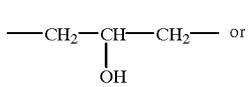     (Ia)

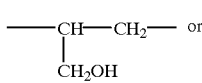     (Ib)

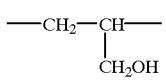     (Ic)

$R_F$ represents a perfluorinated, linear or branched $C_4$–$C_{20}$ alkyl radical $R_H$ represents a linear or branched $C_{23}$–$C_{36}$ alkyl radical n is between 0 and 4;

X represents O, S, S or S; and

-continued

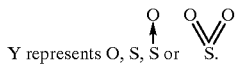
Y represents O, S, S or S.

4. A cosmetic treatment process, comprising applying to the skin, hair or nails a cosmetic composition as defined in claim 3.

5. A cosmetic composition according to claim 4 which is in the form of a milk or cream, oily or oleoalcoholic lotion, oily or oleoalcoholic gel, ionic or non-ionic amphiphilic lipid based vesicular dispersion, solid stick, paste, spray or aerosol foam.

6. A cosmetic composition according to claim 4 which is in the form of a milk or cream for skin or hair, a make-up removing cream, lotion or milk, a sun protection gel or lotion, a shaving foam, an aftershave lotion, a shampoo or conditioner, a body deodorant, a toothpaste, a lacquer, a styling gel, a direct hair dye composition, a hair perming composition, a make-up for eyelashes, eyebrows, nails, lips or skin, a foundation, lipstick, eye-shadow, blusher, eyeliner, mascara, a lip care product or a nail care product.

7. A cosmetic composition according to claim 4 which contains 0.1% to 25% by weight of the compound of formula (I).

8. A cosmetic composition according to claim 4 which contains one or more additives selected from the group consisting of fatty substances, organic solvents, silicones, thickeners, softeners, UV-A or UV-B or broad spectrum solar filters, anti-foaming agents, moisturising agents, humectants, fragrances, preservatives, surfactants, fillers, sequestrating agents, emulsifiers, anionic, cationic, non-ionic or amphoteric polymers and their mixtures, antiperspirants, alkalinizing agents, dyes, pigments, propellants, anti-oxidizing agents and free radical absorbers.

9. A cosmetic composition according to claim 6, which is in the form of a sun protection cream or milk, a shaving cream, or an epidermal treatment cream.

* * * * *